United States Patent
Cohen et al.

(10) Patent No.: US 10,139,461 B2
(45) Date of Patent: Nov. 27, 2018

(54) ANALYSIS OF NUCLEAR MAGNETIC RESONANCE SPECTRA WITH NON-STATIONARY PEAKS

(71) Applicant: Aspect Imaging Ltd., Shoham (IL)

(72) Inventors: Tal Cohen, Herzlia (IL); Uri Rapoport, Moshav Ben Shemen (IL)

(73) Assignee: ASPECT IMAGING LTD., Shoham (IL)

( * ) Notice: Subject to any disclaimer, the term of this patent is extended or adjusted under 35 U.S.C. 154(b) by 121 days.

(21) Appl. No.: 15/465,317

(22) Filed: Mar. 21, 2017

(65) Prior Publication Data

US 2017/0356974 A1 Dec. 14, 2017

Related U.S. Application Data

(60) Provisional application No. 62/349,994, filed on Jun. 14, 2016, provisional application No. 62/393,354, filed on Sep. 12, 2016.

(51) Int. Cl.
*G01V 3/00* (2006.01)
*G01R 33/46* (2006.01)
*G01R 33/485* (2006.01)
*G06F 17/10* (2006.01)
(Continued)

(52) U.S. Cl.
CPC ......... *G01R 33/46* (2013.01); *G01R 33/0064* (2013.01); *G01R 33/12* (2013.01); *G01R 33/485* (2013.01); *G06F 17/10* (2013.01)

(58) Field of Classification Search
USPC ....................................................... 324/307
See application file for complete search history.

(56) References Cited

U.S. PATENT DOCUMENTS 4,694,250 A    9/1987  Iwaoka et al.
6,011,392 A    1/2000  Zhou et al.
6,781,375 B2   8/2004  Miyazaki et al.
(Continued)

OTHER PUBLICATIONS

Norris et al., Online Motion Correction for Diffusion-Weighted Imaging Using Navigator Echoes: Application to RARE Imaging Without Sensitivity Loss, Magnetic Resonance in Medicine, 2001, 45:729-733.
(Continued)

*Primary Examiner* — Rodney E Fuller
(74) *Attorney, Agent, or Firm* — Pearl Cohen Zedek Latzer Baratz LLP (57) ABSTRACT

A method of determining a NMR prediction result of a sample is provided. The method can include receiving a NMR spectrum of the sample and/or identifying a section of a ppm range in the NMR spectrum having a non-stationary peak. The method can include determining a modified data point for the NMR spectrum based on data points in the identified section. The modified data point can be determined such that the modified data point is a weighted average value of the data points in the identified section in the NMR spectrum. The method can include replacing the identified section in the NMR spectrum with the modified data point for the NMR spectrum to determine a modified NMR spectrum. The method can include determining the NMR prediction result of the sample based on the modified NMR spectrum and a calibration vector (e.g., using a partial least square (PLS) analysis).

9 Claims, 5 Drawing Sheets

(51) Int. Cl.
*G01R 33/00* (2006.01)
*G01R 33/12* (2006.01)

(56) References Cited

U.S. PATENT DOCUMENTS

| | | |
|---|---|---|
| 7,715,899 B2 | 5/2010 | Harvey et al. |
| 8,593,141 B1 | 11/2013 | Radparvar et al. |
| 9,041,393 B2 * | 5/2015 | Warntjes ............ G01R 33/5602 324/307 |
| 2002/0149366 A1 | 10/2002 | Asano et al. |
| 2003/0229456 A1 * | 12/2003 | Beger .................. G06F 19/704 702/27 |
| 2007/0249929 A1 | 10/2007 | Jeong et al. |
| 2007/0276221 A1 | 11/2007 | Warntjes |
| 2013/0178734 A1 | 7/2013 | Wald et al. |
| 2014/0296695 A1 * | 10/2014 | He ...................... G01R 33/485 600/410 |
| 2015/0077102 A1 | 3/2015 | Mandal et al. |
| 2016/0321424 A1 | 11/2016 | Otovos et al. |

OTHER PUBLICATIONS

Ting et al., Thin-section MR Imaging of rat brain at 4.7T, JMRI 1992; 2:393-399.

* cited by examiner

ANALYSIS OF NUCLEAR MAGNETIC RESONANCE SPECTRA WITH NON-STATIONARY PEAKS

CROSS REFERENCE TO RELATED APPLICATIONS

This application claims priority to U.S. Provisional Application No. 62/349,994 filed on Jun. 14, 2016 and to U.S. Provisional Application No. 62/393,354 filed on Sep. 12, 2016, all of which are incorporated herein by reference in their entireties.

FIELD OF THE INVENTION

The present invention relates to the field of chemometrics, and more particularly, to nuclear magnetic resonance (NMR) spectroscopy.

BACKGROUND OF THE INVENTION

A chemometrics approach to analysis of NMR spectra can employ analysis techniques (e.g., partial least squares (PLS) regression) to relate a parameter (e.g., pH, density, concentration, boiling point and/or temperature) of a sample to NMR spectra. For example, a calibration model (e.g., calibration vector) can be used to analyze a NMR spectrum of a sample (e.g., using PLS) to determine a NMR prediction of the sample.

The calibration model and/or the calibration vector can be developed in a calibration stage. In the calibration stage, samples that are measured are typically of a known sample type (e.g., organic molecules, proteins and/or nuclei acids). Parameters of a multiple samples of the same sample type and/or corresponding NMR spectra of the multiple samples of the same sample type can be measured and/or analyzed (e.g., using PLS) to determine the calibration model and/or the calibration vector. The calibration model and/or the calibration vector can include values that can relate the measured parameters of the multiple samples to the corresponding measured NMR spectra.

NMR spectra are typically characterized by peaks at particular positions along the spectrum that are not influenced (or substantially not influenced) by environmental conditions (e.g., pH of a solvent that dissolves the sample, temperature of the solvent and/or measurement chamber of an NMR device, etc.). In some scenarios, the environmental conditions can cause the peaks to vary in position along the NMR spectrum. For example, a changing pH of the environment can cause the peaks to vary. Current methods of handling such cases can involve removing the peaks, whose position can vary depending on the environmental conditions and/or ignoring them in an analysis (e.g., PLS analysis of the NMR spectra). In these current methods, the remaining peaks (e.g., peaks that were not removed) can be analyzed with respect to their absolute values, ignoring the canceled-out peaks.

One disadvantage of these current methods can include ignoring important information that can be included in the ignored portions of the spectrum. Another disadvantage of these current methods can include restricting the analysis to use only absolute values of the remaining peaks, thereby, for example, making the analysis and/or the measurement results (e.g., determined parameters of a measured sample) sensitive to errors resulting from electronic parameters and/or other errors which are not canceled out by using relative values.

SUMMARY OF THE INVENTION

One aspect of the present invention provides a method of determining a NMR prediction result of a sample, the method includes: receiving a plurality of NMR spectra and a corresponding plurality of predetermined measured parameters, wherein each of the plurality of NMR spectra corresponds to one of the plurality of predetermined measured parameters; identifying a section of a ppm range in each of the plurality of NMR spectra having a non-stationary peak; determining a modified data point for each of the plurality of NMR spectra based on its respective data points in the identified section of the ppm range such that the modified data point being a weighted average value of the respective data points in the identified section; replacing the identified section of the ppm range in each of the plurality of NMR spectra with its respective determined modified data point to generate a corresponding plurality of modified NMR spectra; determining a modified calibration vector based on the plurality of modified NMR spectra and the plurality of predetermined measured parameters; receiving a measured NMR spectrum of the sample; identifying a section of a ppm range in the measured NMR spectrum having a non-stationary peak; determining a modified data point for the measured NMR spectrum based on data points in the identified section in the measured NMR spectrum such that the modified data point for the measured NMR spectrum being a weighted average value of the data points in the identified section in the measured NMR spectrum; replacing the identified section in the measured NMR spectrum with the modified data point for the measured NMR spectrum to determine a modified measured NMR spectrum; and determining the NMR prediction result of the sample based on the modified measured NMR spectrum and the modified calibration vector.

In some embodiments, the modified calibration vector and the NMR prediction result of the sample are further determined by applying at least one of: partial least square (PLS) analysis, principal component regression (PCR) analysis, neutral network analysis, or any combination thereof to the plurality pf modified NMR spectra and the modified measured NMR spectrum, respectively.

In some embodiments, the method further includes adding to each of the plurality of modified NMR spectra at least one additional data point that represents additional data and adding to the modified measured NMR spectrum corresponding at least one additional data point.

In some embodiments, the additional data point includes at least one of: additional measurements, measurement conditions and external data.

Another aspect of the present invention provides a system for determining a NMR prediction result of a sample, the system includes: an nuclear magnetic resonance (NMR) device to generate at least one NMR spectrum of the sample in a fixed measurement volume; and at least one processing unit to: receive a plurality of NMR spectra and a corresponding plurality of predetermined measured parameters, wherein each of the plurality of NMR spectra corresponds to one of the plurality of predetermined measured parameters; determine a modified data point for each of the plurality of NMR spectra based on data points in an identified section of a ppm range in respective NMR spectrum, identified as having a non-stationary peak, such that the modified data point being a weighted average value of the respective data points in the identified section; replace the identified section of the ppm range in each of the plurality of NMR spectra with its respective determined modified data point to generate the corresponding plurality of modified NMR spectra; determine a modified calibration vector based on the plurality of modified NMR spectra and the plurality of predetermined measured parameters; receive a measured NMR spectrum of the sample; determine a modified data point for the measured NMR spectrum based on data points in an identified section of a ppm range in the measured NMR spectrum, identified as having a non-stationary peak, such that the modified data point for the measured NMR spectrum being a weighted average value of the data points in the identified section in the measured NMR spectrum; replace the identified section in the measured NMR spectrum with the modified data point for the measured NMR spectrum to determine a modified measured NMR spectrum; and determine the NMR prediction result of the sample based on the modified measured NMR spectrum and the modified calibration vector.

In some embodiments, the at least one processing unit is further to identify the section of the ppm range in each of the plurality of NMR spectra and in the measured NMR spectrum having the non-stationary peak.

In some embodiments, the modified calibration vector and the NMR prediction result of the sample are further determined by applying at least one of: partial least square (PLS) analysis, principal component regression (PCR) analysis, neutral network analysis, or any combination thereof to the plurality pf modified NMR spectra and the modified measured NMR spectrum, respectively.

In some embodiments, each of the plurality of modified NMR spectra includes at least one additional data point that represents additional data and the modified measured NMR spectrum comprises corresponding at least one additional data point.

In some embodiments, the additional data point includes at least one of: additional measurements, measurement conditions and external data.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Figure 1A:
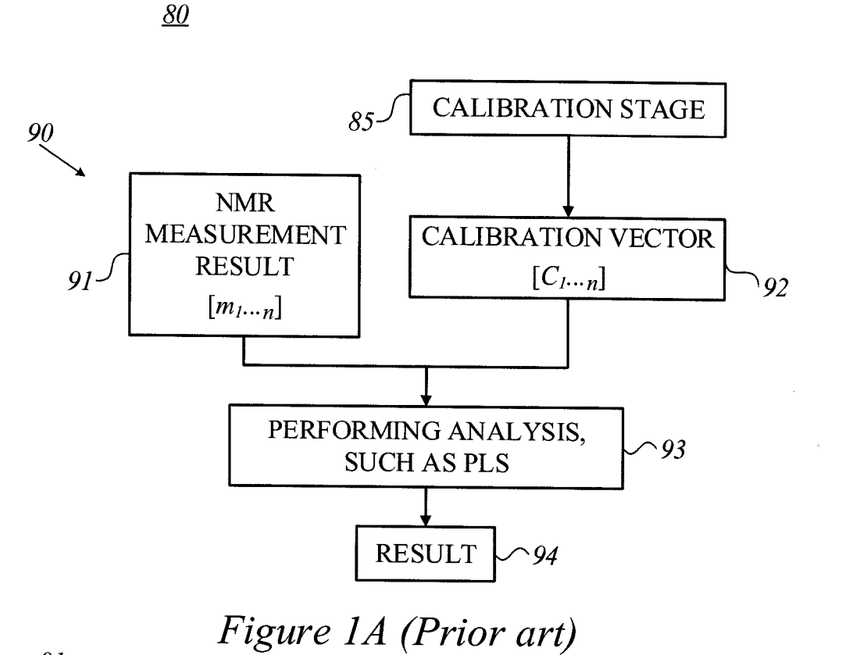
FIG. 1A is a flowchart of a method of NMR analysis, according to an example of prior art.

FIG. 1A is a flowchart of a method 80 of NMR analysis, according to an example of prior art. Method 80 can include executing a calibration stage 85. Calibration stage 85 can receive an input of k NMR spectra obtained from NMR measurements of a set of corresponding k samples of a same sample type whose parameters are known (e.g., predetermined measured parameters), where k is an integer greater than zero. Examples of the predetermined measured parameters of the sample can include pH, density, concentration, temperature, boiling point, Reid vapor pressure (RVP) and/or octane number (research octane number, RON, or motor octane number, MON).

Each of the k NMR spectra can be expressed by n data points, where n is an integer greater than zero. The received data (e.g., k NMR spectra each represented by n data points) can be expressed as a matrix $$[x_1^1 \overset{\ldots}{\ldots} \overset{k}{n}],$$

where x contains the data points of the received k NMR spectra.

Calibration stage 85 can also receive k predetermined measured parameters of the corresponding set of k samples that can be expressed as a vector $[y_{1 \ldots k}]$, where y contains the values of the predetermined measured parameters of the samples.

Calibration stage 85 can include determining a calibration vector and/or a corresponding calibration model $[C_{1 \ldots n}]$ 92 by applying an analysis (e.g., partial least squares (PLS)) to the k NMR spectra and the k predetermined measured parameters.

$$\text{Calibration stage:} \begin{bmatrix} x_1^1 & \ldots & x_n^1 \\ \vdots & \ddots & \vdots \\ x_1^k & \ldots & x_n^k \end{bmatrix} \overset{PLS}{\Leftrightarrow} \begin{bmatrix} y_1 \\ \vdots \\ y_k \end{bmatrix} \overset{yields}{\longrightarrow} [C_1 \ldots C_n]$$

Method 80 can also include executing an analysis stage 90. Analysis stage 90 can include receiving a measured NMR spectrum (e.g., NMR spectrum) 91 of a NMR measurement of sample expressed by n data points, $[m_{1 \ldots n}]$, where m contains the data points.

The analysis stage 90 can include an analysis (e.g., PLS) 93 of measured NMR spectrum $[m_{1 \ldots n}]$ 91 with respect to calibration vector $[C_{1 \ldots n}]$ 92 to yield a NMR prediction result 94 that can be one of parameters of the sample (e.g., pH, density, concentration, temperature, etc.).

$$\text{Analysis stage:} \ [m_1 \ \ldots \ m_n] \overset{PLS}{\Leftrightarrow} \begin{bmatrix} C_1 \\ \vdots \\ C_n \end{bmatrix} \overset{yields}{\longrightarrow} \text{Result}$$

Figure 1B:
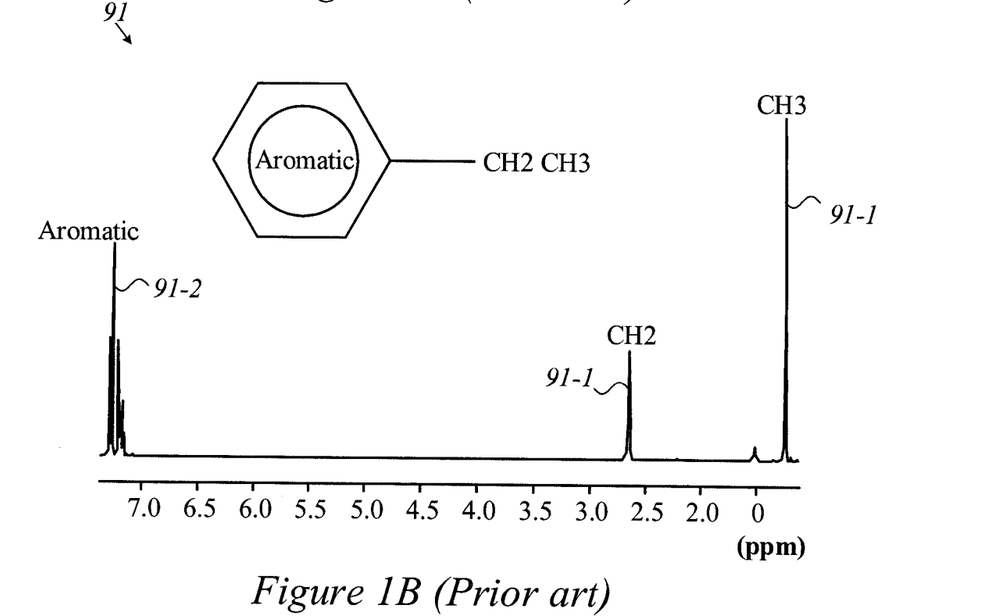
FIG. 1B presents illustration of an example of a graph of 1H NMR spectrum of ethylbenzene, according to an example of the prior art.

FIG. 1B presents illustration of an example of a graph of 1H NMR spectrum 91 of ethylbenzene, according to an example of the prior art. NMR spectrum 91 can have a chemical shift (e.g., peaks 91-1 and 91-2 representing resonance frequencies of specific bonds in ethylbenzene) along a f1 (isotropic) dimension. The position of $C_6H_5$ peak 91-2 can be stationary and not influenced by environmental conditions. The position of $CH_2$ and $CH_3$ peaks 91-1 can be non-stationary and/or can be influenced by environmental conditions as described above.

Figure 1C:
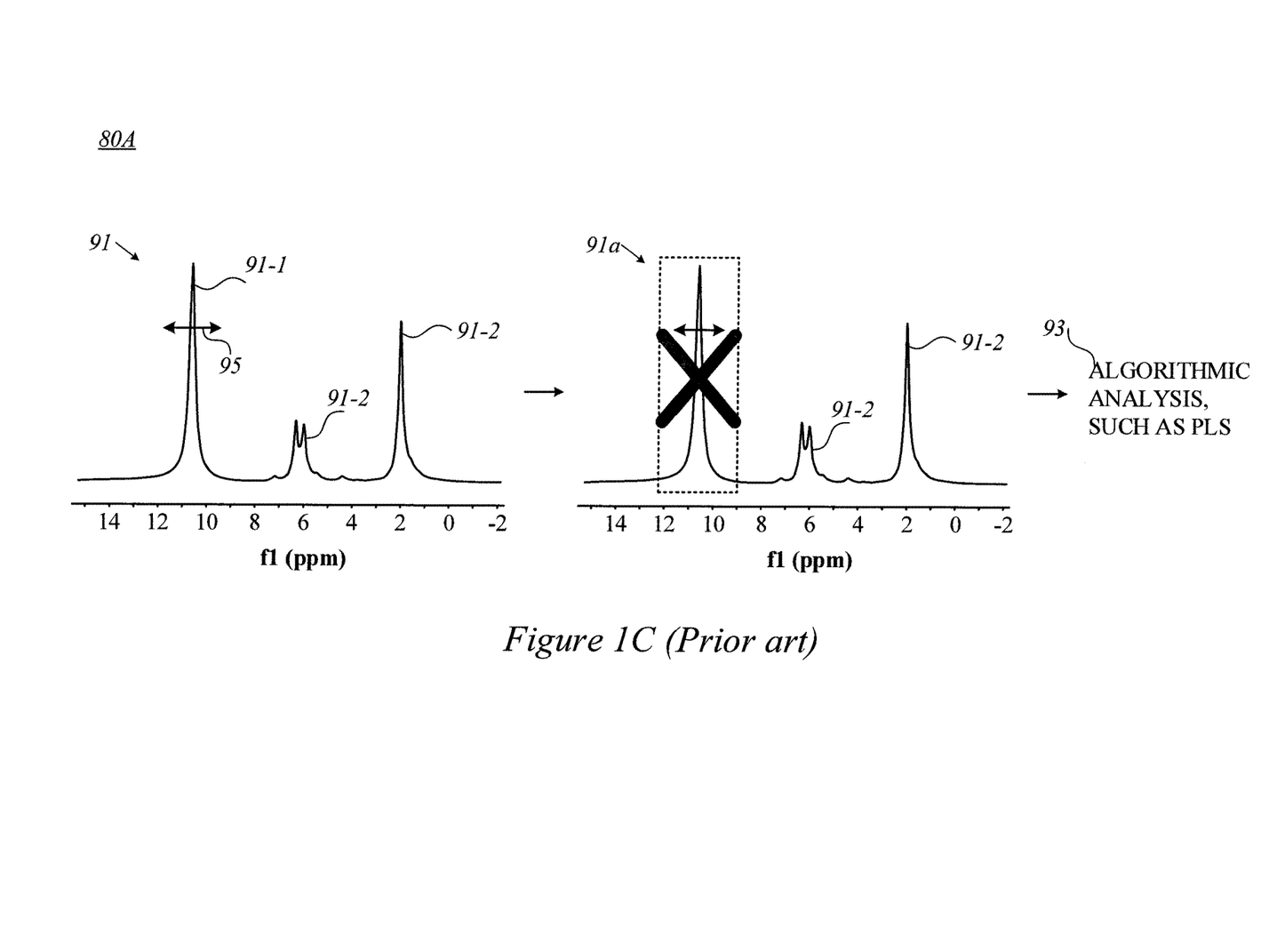
FIG. 1C presents illustrations of a graph of a NMR spectrum that exhibits a peak whose position varies dependent on environmental parameters and a graph of NMR spectrum exhibiting the peak removed, according to an example of the prior art.

FIG. 1C presents illustrations of a graph of a NMR spectrum 91 that exhibits a peak 91-1 whose position varies dependent on environmental parameters and a graph 91A of NMR spectrum 91 exhibiting the peak 91-1 removed, according to an example of the prior art.

Current methods 80 of handling non-stationary peaks 91-1 can include removing peaks 91-1 and ignoring them in an analysis (e.g., PLS) 93. The remaining stationary peaks 91-2 can be analyzed with respect to their absolute values, ignoring the canceled-out non-stationary peaks. For example, in NMR spectrum 91 having a non-stationary peak 91-1, which can move (e.g., depending on sample and/or environmental conditions) within an estimated range 95 and stationary peaks 91-2, current methods 80 can remove the region of non-stationary peak 91-1 (denoted in partial spectrum 91A, deletion marked by "X") and conduct, for example, PLS analysis 93 using partial spectrum 91A.

Some difficulties with current method 80 can include restriction of the analysis to use only absolute values of stationary peaks 91-2 (as removing non-stationary peak(s) 91-1 prohibits normalization procedures), thereby limiting analysis 93 significantly, e.g., making the analysis sensitive to errors resulting from electronic parameters and other global errors which are not canceled out by using relative values. In fact, when general measurement characteristics modify all peaks, ignoring non-stationary peak(s) 91-1 can prevent detecting these general measurement characteristics as a source for a systematic error. Another difficulty with current method 80 can include ignoring important information that can be included in the ignored portions 95 of the spectrum that include non-stationary peaks 91-1 (e.g., as shown in FIG. 1C).

It is noted that while the analysis is exemplified herein by PLS analysis, can include other analysis methods, such as PCR (principal component regression) analysis and/or neural network analysis.

While illustrated spectra 91 are shown as NMR spectra it is explicitly noted that chemometrics as well as the disclosed invention can also refer to and be applied to spectra derived from other analyzers such as infrared (IR), e.g., near infrared (NIR) spectrometers, Raman spectrometers etc.

Figure 2:
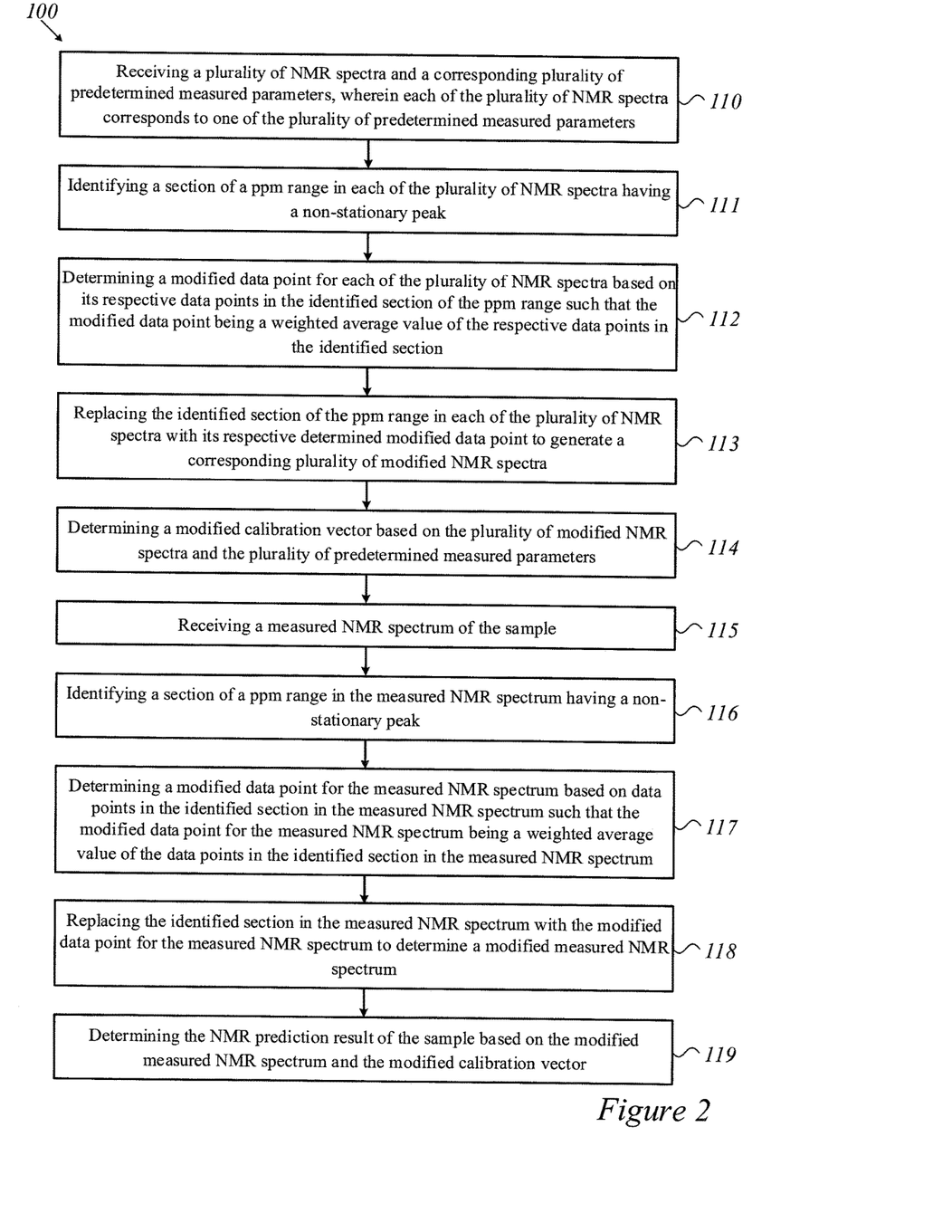
FIG. 2 is a flowchart of a method of determining a NMR prediction result of a sample, according to some embodiments of the invention.

FIG. 2 is a flowchart of a method 100 of determining a NMR prediction result of a sample.

Method 100 can include receiving 110 a plurality of NMR spectra and a corresponding plurality of predetermined measured parameters, wherein each of the plurality of NMR spectra corresponds to one of the plurality of predetermined measured parameters.

Figure 3:
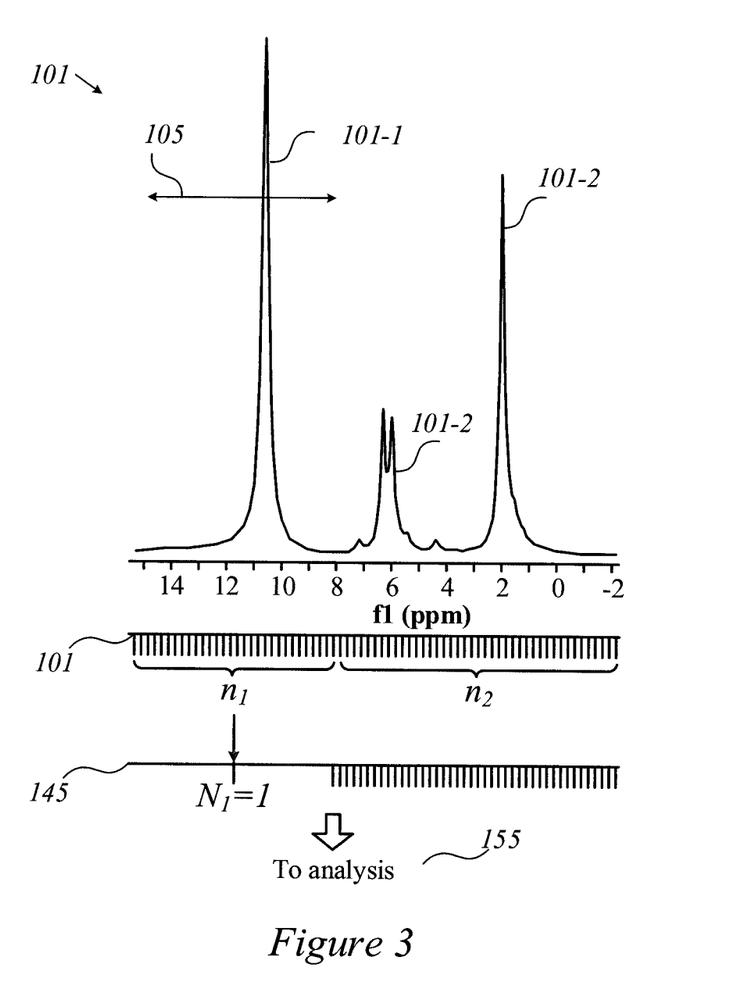
FIG. 3 is an illustration of a graph of a NMR spectrum and graphs showing representative data points of NMR spectrum, according to some embodiments of the invention.

For example, method 100 can receive k NMR spectra (e.g., calibration NMR spectra), each expressed by n data points (e.g., as shown in FIG. 3), obtained from NMR measurements of a set of corresponding k samples whose parameters are known (e.g., predetermined measured parameters), and k predetermined measured parameters (e.g., certified lab results), where k and n are integers greater than zero. The received k NMR spectra can be expressed as a matrix $[x_{1 \ldots n}^{1 \cdots k}]$, where x contains data points, and/or the received k predetermined measured parameters can be expressed as a vector $[y_{1 \ldots k}]$, where y contains the values of the predetermined measured parameters. Each of k NMR spectra can correspond to one of predetermined measured parameters. For example, NMR spectrum $[x_{1 \ldots n}^3]$ can correspond to predetermined measured parameter $[y_3]$.

In each of k NMR spectra, the n data points can include $n_1$ data points from section having non-stationary peak (e.g., section 105 and/or peak 101-1 as shown in FIG. 3) and/or $n_2$ data points from section having stationary peaks (e.g., peaks 101-2 as shown in FIG. 3), where $n=n_1+n_2$.

Method 100 can include identifying 111 a section of a ppm range in each of the plurality of NMR spectra having a non-stationary peak. For example, in each of k NMR spectra, a section 105 that includes the $n_1$ data points (e.g., as shown in FIG. 3) as described above can be identified.

Method 100 can include determining 112 a modified data point for each of the plurality of NMR spectra based on its respective data points in the identified section of the ppm range such that the modified data point being a weighted average value of the respective data points in the identified section. For example, $N_1=1$ modified data point (e.g., as shown in FIG. 3) for each of k NMR spectra can be determined based on respective identified $n_1$ data points in respective NMR spectrum. The $N_1$ modified data point can include a weighted average value (e.g., stationary weighted peak) of respective identified $n_1$ data points in the identified section.

Method 100 can include replacing 113 the identified section of the ppm range in each of the plurality of NMR spectra with its respective determined modified data point to generate a corresponding plurality of modified NMR spectra. For example, the identified $n_1$ data points in each of k NMR spectra can be replaced by the respective $N_1$ modified data point to determine k corresponding modified NMR spectra (e.g., NMR spectrum 145 as shown in FIG. 3).

In some embodiments, the modified data point $N_1$ (e.g., stationary weighted peak) for each of k NMR spectra is determined to provide a correct normalization of the corresponding modified NMR spectrum (e.g., NMR spectrum 145 as shown in FIG. 3). In some embodiments, the correct normalization of the modified NMR spectrum (e.g., NMR spectrum 145 as shown in FIG. 3) can provide data concerning stationary peaks in the NMR spectrum. In some embodiments, two or more modified data points are determined (e.g., $N_1 \geq 1$).

In some embodiments, method 100 includes adding to each the plurality of modified NMR spectra at least one additional data point that represents additional data. The additional data can include at least one of: additional measurements, measurement conditions and/or external data. For example, additional M ($M \geq 1$) data points can be added to each of k modified NMR spectra to provide $[x_{1 \ldots N}^{1 \cdots k}]$, where $N = N_1 + n_2 + M$.

Method 100 can include determining 114 a modified calibration vector based on the plurality of modified NMR spectra and the plurality of predetermined measured parameters. For example, the modified calibration vector $[C_{1 \ldots N}]$ and/or model (e.g., a calibration stage) can be determined based on k modified NMR spectra $[x_{1 \ldots N}^{1 \cdots k}]$ and k predetermined measured parameters $[y_{1 \ldots k}]$.

$$\text{Calibration stage:} \begin{bmatrix} x_1^1 & \cdots & x_N^1 \\ \vdots & \ddots & \vdots \\ x_1^k & \cdots & x_N^k \end{bmatrix} \overset{PLS}{\Leftrightarrow} \begin{bmatrix} y_1 \\ \vdots \\ y_k \end{bmatrix} \overset{yields}{\longrightarrow} [C_1 \ldots C_N]$$

Advantageously, this approach causes the method to produce a robust modified calibration vector $[C_{1 \ldots N}]$.

Method 100 can include receiving 115 a measured NMR spectrum of the sample. For example, method 100 can receive the measured NMR spectrum $[m_{1 \ldots n}]$ expressed by n data points (e.g., spectrum 101 as shown in FIG. 3), obtained from NMR measurement of the sample. The n data points can include $n_1$ data points from section having non-stationary peaks (e.g., peak 101-1 as shown in FIG. 3) and/or $n_2$ data points from section having stationary peaks (e.g., peaks 101-2 as shown in FIG. 3), where $n = n_1 + n_2$ (e.g., as described above with respect to stage 110).

Method 100 can include identifying 116 a section of a ppm range in the measured NMR spectrum having a non-stationary peak (e.g., as described above with respect to stage 111).

Method 100 can include determining 117 a modified data point for the measured NMR spectrum based on data points in the identified section in the measured NMR spectrum such that the modified data point for the measured NMR spectrum being a weighted average value of the data points in the identified section in the measured NMR spectrum (e.g., as described above with respect to stage 112). For example, $N_1 = 1$ modified data point (e.g., as shown in FIG. 3) can be determined based on the identified $n_1$ data points in the measured NMR spectrum. The $N_1$ modified data point can include a weighted average value (e.g., stationary weighted peak) of the identified $n_1$ data points in the identified section in the measured NMR spectrum $[m_{1 \ldots n}]$. In some embodiments, two or more modified data points are determined (e.g., $N_1 \geq 1$).

In some embodiments, method 100 includes adding to the modified measured NMR spectrum at least one additional data point that represents additional data. The additional data can include at least one of: additional measurements, measurement conditions and/or external data. For example, additional M ($M \geq 1$) data points can be added to the modified NMR spectrum to provide $[m_{1 \ldots N}]$ where $N = N_1 + n_2 + M$.

Method 100 can include replacing 118 the identified section in the measured NMR spectrum with the modified data point for the measured NMR spectrum to determine a modified measured NMR spectrum (e.g., as described above with respect to stage 113).

Method 100 can include determining 119 the NMR prediction result of the sample based on the modified measured NMR spectrum and the modified calibration vector. For example, the NMR prediction result can be determined based on the modified measured NMR spectrum $[m_{1 \ldots N}]$ and the modified calibration vector $[C_{1 \ldots N}]$ (e.g., an analysis stage).

$$\text{Analysis stage:} \quad [m_1 \ldots m_N] \overset{PLS}{\Leftrightarrow} \begin{bmatrix} C_1 \\ \vdots \\ C_N \end{bmatrix} \overset{yields}{\longrightarrow} \text{Result}$$

In various embodiments, the modified calibration vector (e.g., $[C_{1 \ldots N}]$) and the NMR prediction result of the sample are further determined by applying at least one of: partial least square (PLS) analysis, principal component regression (PCR) analysis, neutral network analysis, or any combination thereof to the plurality pf modified NMR spectra (e.g., $[x_{1 \ldots N}^{1 \cdots k}]$) and the modified measured NMR spectrum ($[m_{1 \ldots N}]$), respectively One advantage of method 100 can include taking into account regions 105 with non-stationary peaks 101-1 by determining the modified data point (e.g., stationary weighted peak) to provide correct normalization of the modified NMR spectrum that provides relative data concerning stationary peaks in the NMR spectrum, thus retaining at least some of the information in these regions.

FIG. 3 is an illustration of a graph of a NMR spectrum and graphs showing representative data points of NMR spectrum 101, according to some embodiments of the invention. NMR spectrum 101 can include, for example, a stationary peak which does not change its position in f1 axis and/or is not influenced (or substantially not influenced) by environmental conditions (e.g., peak 101-2 on 2 ppm, as shown in FIG. 3) and/or non-stationary peaks that can be influence by environmental conditions (e.g., peak 101-1, as shown in FIG. 3). The full ppm range of NMR spectrum 101 (e.g., 15 ppm to −2 ppm) can be divided to multiple sections, where each section can be integrated into n integrals (e.g., $[m_{1 \ldots n}]$, where m includes data points and where n=1700) and/or normalized to represent the integration section having stationary peaks 101-2 represented by $n_2$ (e.g., $n_2$=1000) data points (e.g., section 15 ppm to −2 ppm) and the integration section having non-stationary peak(s) 101-1 represented by $n_1$ (e.g., $n_1$=700) data points (e.g., section 15 ppm to 8 ppm). These sections can be identified in stage 111 and/or stage 116 of method 100.

The integration sections having non-stationary peaks represented by $n_1$ data points can be integrated (e.g., in stage 112 and/or stage 117 of method 100), for example, into a single modified data point $N_1=1$ (e.g., the modified data point includes weighted average value of the $n_1$ data points). Accordingly, modified NMR spectrum 145 (e.g., determined in stage 140 of method 100 by replacing the identified $n_1$ data points by the single $N_1$ modified data point) can include $N=1001$ normalized integration sections (e.g., $N_1=1$, $n_2=1000$ such that $N=N_1+n_2=1001$).

Modified NMR spectrum 145 (e.g., $[m_1 \ldots _N]$ with $N=n_2+N=1001$) can be processed by analysis (e.g., PLS) 155 to enable full analysis of the results—maintaining the overall ratio between the stationary peaks 101-2 not sensitive to the f1 (ppm) position of non-stationary peak(s) 101-1 and thus avoiding the current method 80 need to use absolute values only of stationary peaks.

Figure 4:
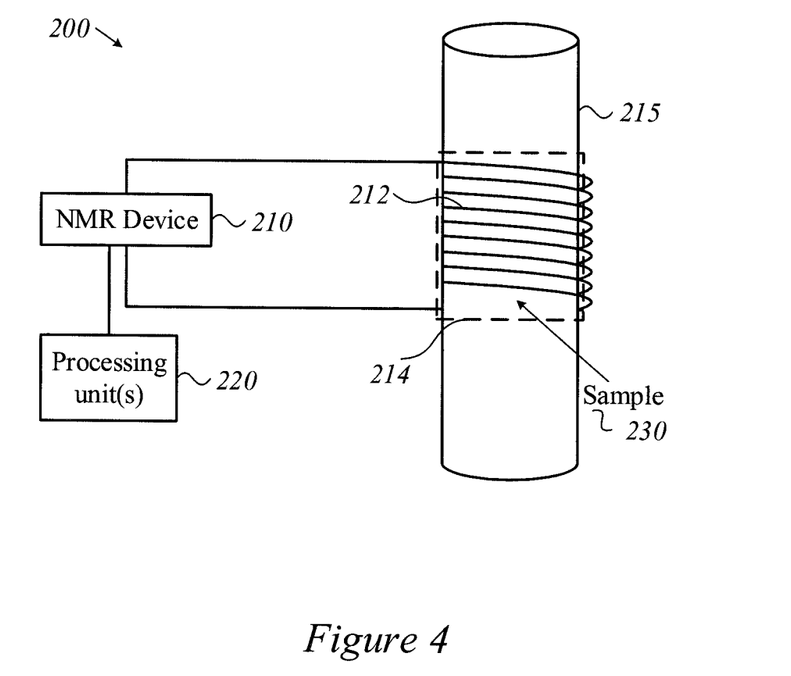
FIG. 4 is a schematic illustration of a system for determining a NMR prediction result of a sample, according to some embodiments of the invention.

FIG. 4 is a schematic illustration of a system 200 for determining a NMR prediction result of a sample, according to some embodiments of the invention. System 200 can carry out stages of method 100. System 200 can include a NMR device 210 (including at least one NMR RF coil 212) that can generate NMR spectrum (e.g., NMR spectrum 101) of the sample 230 in a fixed measurement volume 214. Sample 230 can be static or flowing.

System 200 can include at least one processing unit 220 that can: (i) receive a plurality of NMR spectra and a corresponding plurality of predetermined measured parameters, wherein each of the plurality of NMR spectra corresponds to one of the plurality of predetermined measured parameters; (ii) determine a modified data point for each of the plurality of NMR spectra based on data points in an identified section of a ppm range in respective NMR spectrum, identified as having a non-stationary peak, such that the modified data point being a weighted average value of the respective data points in the identified section; (iii) replace the identified section of the ppm range in each of the plurality of NMR spectra with its respective determined modified data point to generate the corresponding plurality of modified NMR spectra; (iv) determine a modified calibration vector based on the plurality of modified NMR spectra and the plurality of predetermined measured parameters; (v) receive a measured NMR spectrum of the sample; (vi) determine a modified data point for the measured NMR spectrum based on data points in an identified section of a ppm range in the measured NMR spectrum, identified as having a non-stationary peak, such that the modified data point for the measured NMR spectrum being a weighted average value of the data points in the identified section in the measured NMR spectrum; (vii) replace the identified section in the measured NMR spectrum with the modified data point for the measured NMR spectrum to determine a modified measured NMR spectrum; and/or (viii) determine the NMR prediction result of the sample based on the modified measured NMR spectrum and the modified calibration vector.

In some embodiments, the at least one processing unit is further to identify the section of the ppm range in each of the plurality of NMR spectra and in the measured NMR spectrum having the non-stationary peak.

In some embodiments, the modified calibration vector and the NMR prediction result of the sample are further determined by applying at least one of: partial least square (PLS) analysis, principal component regression (PCR) analysis, neutral network analysis, or any combination thereof to the plurality pf modified NMR spectra and the modified measured NMR spectrum, respectively.

In some embodiments, each of the plurality of modified NMR spectra comprises at least one additional data point that represents additional data and the modified measured NMR spectrum comprises corresponding at least one additional data point. In some embodiments, the additional data point comprises at least one of: additional measurements, measurement conditions and external data.

It is noted that an advantage of NMR analysis is the utilization of the information in the relative peak heights, which is partly due to fixed measurement volume 214 in the NMR measurement method. It is noted that system 200 can be operated with other analyzers such as infrared (IR), e.g., near infrared (NIR) spectrometers and/or Raman spectrometers replacing NMR device 210, with processing unit(s) 220 to analyze the corresponding spectra according to similar guidelines.

One advantage of the disclosed invention can include maintaining the advantage of NMR spectrometry of being able to analyze relative peak values. Taking ethylbenzene ($C_6H_5CH_2CH_3$, e.g., as shown in FIG. 1) as an example, fixed measurement volume 214 of NMR device ensures that the relative peak heights of the hydrogens in the $C_6H_5$, $CH_2$ and $CH_3$ groups maintain a fixed proportion (5:2:3), and any measurement effect influences them similarly. In the case where any one of these peaks is discarded, the information on common effectors can be lost. In the disclosed invention this information is maintained via the incorporation of the modified measurement values (e.g., stationary weighted peaks) in modified NMR spectrum (e.g., modified NMR spectrum 145, as shown in FIG. 3), which express the relative information carried by non-stationary peak(s) 101-1.

Another advantage of the disclosed invention can include incorporating additional information related to non-stationary peak(s) 101-1 via the additional M data points, where the additional M data points can include any characteristic of the non-stationary peak (height, movement, etc., now entered as an external data point) as well as information relating to the measurement conditions and/or additional measurements by other devices (e.g., an IR spectrometer)—can be used to further improve the efficiency and accuracy of analysis (e.g., algorithmic analysis) 150.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A method of determining a NMR prediction result of a sample, the method comprising:
   receiving a plurality of NMR spectra and a corresponding plurality of predetermined measured parameters, wherein each of the plurality of NMR spectra corresponds to one of the plurality of predetermined measured parameters;
   identifying a section of a ppm range in each of the plurality of NMR spectra having a non-stationary peak;
   determining a modified data point for each of the plurality of NMR spectra based on its respective data points in the identified section of the ppm range such that the modified data point being a weighted average value of the respective data points in the identified section;
   replacing the identified section of the ppm range in each of the plurality of NMR spectra with its respective determined modified data point to generate a corresponding plurality of modified NMR spectra;
   determining a modified calibration vector based on the plurality of modified NMR spectra and the plurality of predetermined measured parameters;
   receiving a measured NMR spectrum of the sample;
   identifying a section of a ppm range in the measured NMR spectrum having a non-stationary peak;
   determining a modified data point for the measured NMR spectrum based on data points in the identified section in the measured NMR spectrum such that the modified data point for the measured NMR spectrum being a weighted average value of the data points in the identified section in the measured NMR spectrum;
   replacing the identified section in the measured NMR spectrum with the modified data point for the measured NMR spectrum to determine a modified measured NMR spectrum; and
   determining the NMR prediction result of the sample based on the modified measured NMR spectrum and the modified calibration vector.

2. The method of claim 1, wherein the modified calibration vector and the NMR prediction result of the sample are further determined by applying at least one of: partial least square (PLS) analysis, principal component regression (PCR) analysis, neutral network analysis, or any combination thereof to the plurality pf modified NMR spectra and the modified measured NMR spectrum, respectively.

3. The method of claim 1, further comprising adding to each of the plurality of modified NMR spectra at least one additional data point that represents additional data and adding to the modified measured NMR spectrum corresponding at least one additional data point.

4. The method of claim 3, wherein the additional data point comprises at least one of:
   additional measurements, measurement conditions and external data.

5. A system for determining a NMR prediction result of a sample, the system comprising:
   an nuclear magnetic resonance (NMR) device to generate at least one NMR spectrum of the sample in a fixed measurement volume; and
   at least one processing unit to:
   receive a plurality of NMR spectra and a corresponding plurality of predetermined measured parameters, wherein each of the plurality of NMR spectra corresponds to one of the plurality of predetermined measured parameters;
   determine a modified data point for each of the plurality of NMR spectra based on data points in an identified section of a ppm range in respective NMR spectrum, identified as having a non-stationary peak, such that the modified data point being a weighted average value of the respective data points in the identified section;
   replace the identified section of the ppm range in each of the plurality of NMR spectra with its respective determined modified data point to generate the corresponding plurality of modified NMR spectra;
   determine a modified calibration vector based on the plurality of modified NMR spectra and the plurality of predetermined measured parameters;
   receive a measured NMR spectrum of the sample;
   determine a modified data point for the measured NMR spectrum based on data points in an identified section of a ppm range in the measured NMR spectrum, identified as having a non-stationary peak, such that the modified data point for the measured NMR spectrum being a weighted average value of the data points in the identified section in the measured NMR spectrum;
   replace the identified section in the measured NMR spectrum with the modified data point for the measured NMR spectrum to determine a modified measured NMR spectrum; and
   determine the NMR prediction result of the sample based on the modified measured NMR spectrum and the modified calibration vector.

6. The system of claim 5, wherein the at least one processing unit is further to identify the section of the ppm range in each of the plurality of NMR spectra and in the measured NMR spectrum having the non-stationary peak.

7. The system of claim 5, wherein the modified calibration vector and the NMR prediction result of the sample are further determined by applying at least one of: partial least square (PLS) analysis, principal component regression (PCR) analysis, neutral network analysis, or any combination thereof to the plurality pf modified NMR spectra and the modified measured NMR spectrum, respectively.

8. The system of claim 5, wherein each of the plurality of modified NMR spectra comprises at least one additional data point that represents additional data and the modified measured NMR spectrum comprises corresponding at least one additional data point.

9. The system of claim 8, wherein the additional data point comprises at least one of: additional measurements, measurement conditions and external data.

* * * * *